(12) United States Patent
Azure

(10) Patent No.: US 9,775,671 B2
(45) Date of Patent: *Oct. 3, 2017

(54) MULTI-LAYER ELECTRODE ABLATION PROBE AND RELATED METHODS

(71) Applicant: LaZure Scientific, Inc., Issaquah, WA (US)

(72) Inventor: Larry Azure, LaConner, WA (US)

(73) Assignee: LaZure Scientific, Inc., Issaquah, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/221,504

(22) Filed: Jul. 27, 2016

(65) Prior Publication Data
US 2017/0014179 A1    Jan. 19, 2017

Related U.S. Application Data

(60) Continuation of application No. 14/044,756, filed on Oct. 2, 2013, now Pat. No. 9,603,654, which is a
(Continued)

(51) Int. Cl.
*A61B 18/14* (2006.01)
*A61B 18/18* (2006.01)
(Continued)

(52) U.S. Cl.
CPC .......... *A61B 18/1477* (2013.01); *A61B 18/14* (2013.01); *A61B 18/18* (2013.01); *A61N 1/05* (2013.01); *A61B 2017/00867* (2013.01); *A61B 2018/0016* (2013.01); *A61B 2018/143* (2013.01); *A61B 2018/1407* (2013.01); *A61B 2018/1425* (2013.01);
(Continued)

(58) Field of Classification Search
CPC ................ A61B 18/14; A61B 18/1477; A61B 2018/1425; A61B 2018/124; A61B 2018/126; A61B 2018/1407; A61B 2018/143; A61B 2018/1432; A61B 2018/1435; A61B 2018/1465; A61B 2018/0016; A61B 2018/1475
USPC ............................ 606/34, 41, 42, 46–48, 50
See application file for complete search history.

(56) References Cited

U.S. PATENT DOCUMENTS 5,472,441 A    12/1995    Edwards et al.
5,683,366 A    11/1997    Eggers et al.
(Continued)

OTHER PUBLICATIONS

International Search Report dated Nov. 13, 2008 for International Application No. PCT/US2008/076451.

*Primary Examiner* — Thomas Giuliani
(74) *Attorney, Agent, or Firm* — Wilson Sonsini Goodrich & Rosati

(57) ABSTRACT

Electric field delivery and ablation of target tissue regions, including cancerous cells and solid tumors. Methods and systems include delivering an electric field to a target tissue, and may include positioning a first electrode or plurality to at least partially define a first treatment volume in the target tissue; positioning a second electrode or plurality to at least partially define a second treatment volume, the first volume is disposed in the second volume; and establishing a first current flow extending through the first volume and a second current flow extending through the second volume.

11 Claims, 10 Drawing Sheets

Related U.S. Application Data division of application No. 12/210,942, filed on Sep. 15, 2008, now Pat. No. 8,562,602.

(60) Provisional application No. 60/972,708, filed on Sep. 14, 2007.

(51) Int. Cl.
*A61N 1/05* (2006.01)
*A61B 17/00* (2006.01)
*A61B 18/00* (2006.01)

(52) U.S. Cl.
CPC ............... *A61B 2018/1432* (2013.01); *A61B 2018/1475* (2013.01); *C08L 2201/12* (2013.01)

(56) References Cited

U.S. PATENT DOCUMENTS

| | | | |
|---|---|---|---|
| 6,296,638 B1 | 10/2001 | Davison et al. | |
| 6,330,478 B1 | 12/2001 | Lee et al. | |
| 9,603,654 B2 * | 3/2017 | Azure | A61B 18/14 |
| 2005/0209640 A1 * | 9/2005 | Palti | A61N 1/40 |
| | | | 607/2 |
| 2006/0217707 A1 * | 9/2006 | Daniel | A61B 18/1477 |
| | | | 606/50 |
| 2007/0179494 A1 * | 8/2007 | Faure | A61B 18/1477 |
| | | | 606/41 |
| 2014/0100565 A1 * | 4/2014 | Azure | A61B 18/14 |
| | | | 606/41 |

* cited by examiner

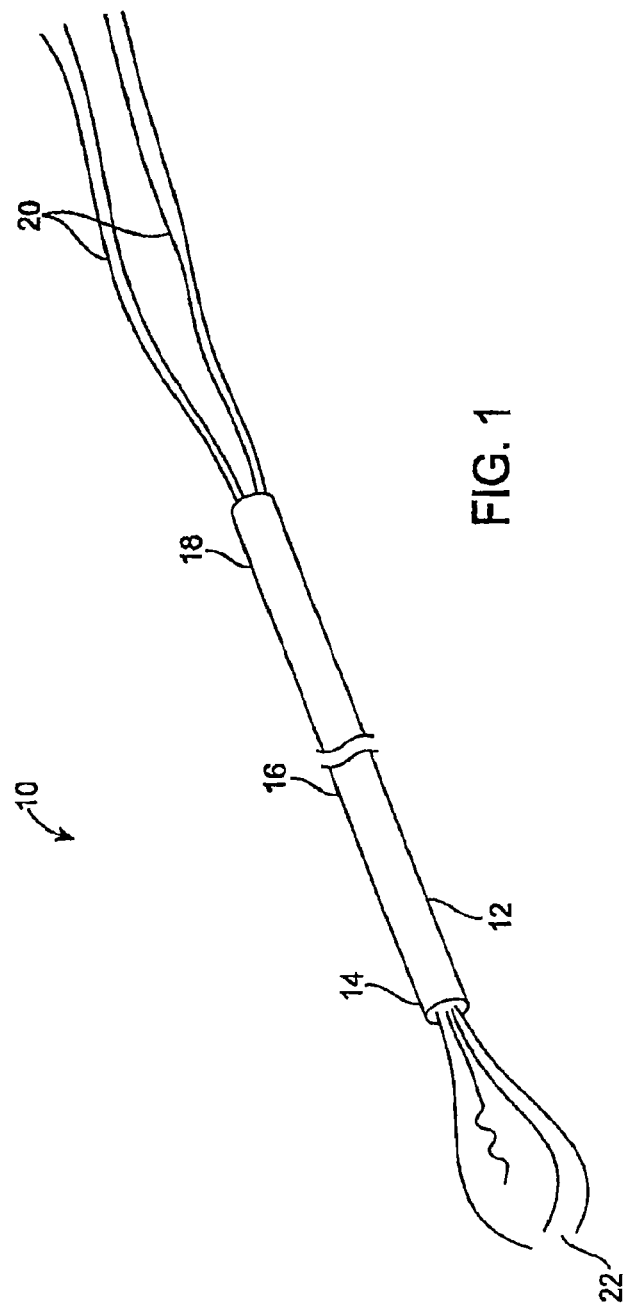

MULTI-LAYER ELECTRODE ABLATION PROBE AND RELATED METHODS

CROSS-REFERENCE

This application is a continuation of application Ser. No. 14/044,756, filed Oct. 2, 2013, now U.S. Pat. No. 9,603,654, issued Mar. 28, 2017, which is a divisional application of Ser. No. 12/210,942, filed Sep. 15, 2008, now U.S. Pat. No. 8,562,602, issued Oct. 22, 2013, which claims the benefit of U.S. Provisional Application No. 60/972,708, filed Sep. 14, 2007, the contents of each of which are incorporated herein by reference.

BACKGROUND OF THE INVENTION

The present invention relates generally to electric field delivery to tissue regions. More specifically, the present invention relates to electric field delivery and ablation of target tissue regions, including cancerous cells and solid tumors, using improved ablation probes.

Several methods of tissue ablation are currently available. Existing techniques of tissue ablation typically rely on high-frequency heat inducing electric current to a tissue of a patient to create a lesion for cutting tissue, removing unwanted tissue (e.g., cancerous tissue), staunch bleeding, and the like. Common hyper-thermal tumor ablation techniques include use of high-frequency radio frequency (RF) or microwave sources to heat tissue in order to mediate heat-induced histological damage to the target tissue. RF thermal ablation techniques include, for example, application of high frequency current to cause ionic agitation and frictional heating to tissues surrounding one or more positioned electrodes. The thermally induced tissue destruction is non-specific to targeted tissue and destroys both healthy and non-healthy tissue. Treatment is typically "targeted" by attempting to limit or control application to a limited or desired region. Controlling treatment delivery in this manner, however, has been difficult and has shown limited success, and often unavoidably results in unwanted destruction of non-target or healthy tissue. More recent techniques, such as irreversible electroporation by application of high-voltage direct current, while more effective in reducing thermally mediated destruction, similarly cause damage and destruction indiscriminately to tissues subjected to treatment.

Thus, there is a need for minimally invasive ablation techniques that more selectively destroy targeted tissue while minimizing damage to non-target tissue.

BRIEF SUMMARY OF THE INVENTION

The present invention provides systems, devices and related methods for applying electric fields for more selective and controllable cancerous cell destruction and tissue ablation. Devices of the present invention will generally be designed to advance an electrode or plurality of electrodes to a target tissue region and apply an electric field to the target tissue region. The electrode or plurality thereof can be positioned such that the applied electric field radiates throughout the target tissue region, including, for example, where the electric field radiates outwardly and in a plurality of directions radially through the target tissue. In certain embodiments, the energy applied to the target tissue region can be selected such that electrically generated heat is minimized and may include application of mild hyperthermia, and undesirable or excessive elevations in tissue temperature can be often be avoided.

The present invention includes methods of delivering an electric field to a target tissue. A method can include, for example, positioning electrodes to define a first treatment volume and a second treatment volume in a target tissue, wherein the first volume is disposed in the second volume; and establishing current flows extending radially within the first volume as well as extending through the second volume.

The present invention further includes devices and systems, including multi-layer electrode ablation devices and probes. A probe can include a plurality of electrodes defining a first treatment volume and a second treatment volume in a target tissue, wherein the first volume is smaller than the second volume and positioned within the second volume. Further included can be an energy source coupled to the probe to establish target tissue ablating current flows extending radially through the first and second volumes.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 1 illustrates a device according to an embodiment of the present invention.

DETAILED DESCRIPTION OF THE INVENTION

Figure 2C:
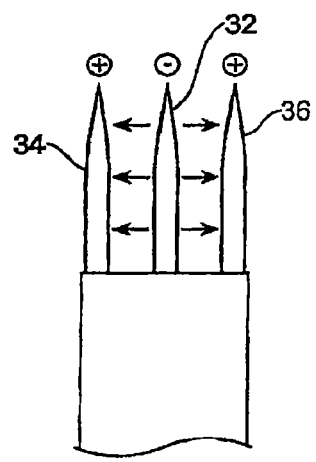
FIGS. 2A through 2D illustrate a device according to another embodiment of the present invention.

The present invention provides systems and devices, and related methods for tissue ablation. According to the present invention, an electrode or plurality of electrodes can be introduced into a target tissue region and an electric field applied to the target tissue region. In some instances, the energy applied to the target tissue region can be selected such that electrically generated heat is minimized and may include induction or delivery of controlled, mild hyperthermia, but where excessive or undesirable rises in tissue temperature can be avoided, thereby providing low-power or non-thermal ablation (e.g., mild hyperthermia) of target cells. Devices and methods of the present invention can effectively ablate cancerous cells without an excessive or undesirable thermal effect being a factor in the ablation process, with ablation occurring primarily among abnormally proliferating cells or cells exhibiting unregulated growth (e.g., cancerous cells). Thus, the present invention is advantageous in providing minimally invasive, selective ablation or destruction of cancerous cells, while leaving normal cells or tissue substantially intact.

The target tissue region can include a mass or solid portion of tissue. Typically, the target tissue region includes cancerous cells including, for example, a target tissue region including a solid tumor. The volume of the tissue to be subject to the inventive methods can vary, and will depend at least partially based on the size of the mass of cancerous cells. Peripheral dimensions of the target tissue region can be regular (e.g., spherical, oval, etc.), or can be irregular. The target tissue region can be identified and/or characterized using conventional imaging methods, and various imaging systems can be used for locating and/or positioning of a device or electrodes of the invention within a patient's tissue or at or within a target tissue region.

Electrodes can be positioned as described and an electric field applied (e.g., alternating electric field). Ablation techniques according to the present invention can be accomplished in some embodiments without an undesirable or excessive increase in local tissue temperature and without high-temperature thermal effects (e.g., average tissue temperature increases substantially above 10 degrees C. body temperature or substantially above about 48 degrees C.) of energy application being a primary means by which tissue ablation occurs. The applied electric field can include a low-intensity, intermediate frequency alternating current. In some embodiments, electrode configuration and field application can take advantage of tumor physiology, including, e.g., orientation of dividing/proliferating cells within a target tissue region, and ensure that the electric field provided is substantially aligned with a division axis of a dividing cancerous cell.

Referring to FIG. 1, a device according to an embodiment of the present invention is described. The device 10 includes a delivery member 12 having a distal portion 14 and a proximal portion 16. The device 10 further includes a proximal portion 18 of the device that can be coupled (e.g., removably coupled) to the delivery member 12. Additionally, the device 10 can include conductive cables 20 electrically coupled to an energy source (not shown). The device includes a plurality of electrodes 22 at the distal portion 14 of the delivery member 12. The electrodes 22 can be positioned or fixed, for example, at the distal end of the delivery member 12 or positionable and deployable from a lumen of the delivery member 12 and retractable in and out of the distal end of the delivery member 12. The electrodes 22 can include a non-deployed state, where the electrodes 22 can be positioned within a lumen of the delivery member 12, and a deployed state when advanced from the distal end of the delivery member 12. Electrodes 22 are advanced out the distal end and distended into a deployed state substantially defining an ablation volume.

The present invention can include a variety of electrode compositions, configurations, geometries, etc. In certain embodiments, electrodes can include tissue-penetrating electrodes including, for example, small diameter metal wires having tissue-piercing or sharpened distal ends that can penetrate tissue as they are advanced within the target tissue region. Electrodes can be non-insulated or can include an insulated portion. In one embodiment, a non-insulated portion of the electrode provides an electric field delivery surface for delivery of electrical current to the surrounding tissue. Electrodes can be substantially rigid, e.g., so as to be more easily advanced through tissue, including hardened or more dense tissue, or can be more flexible, depending upon the desired use. In one embodiment, an electrode includes a needle or needle-like electrode or electrode having a substantially linear portion. In another embodiment, electrodes can be curved, having a curved portion or portion with a radius of curvature. Electrode composition can vary and in certain embodiments can include a memory metal (e.g., commercially available memory metals, Nitinol™ etc.) or sprung steel. Suitable electrode materials can include, e.g., stainless steel, platinum, gold, silver, copper and other electrically conductive materials, metals, polymers, etc. In certain embodiments, electrodes can be positioned in and deployable from a lumen of a catheter and/or microcatheter or other member for introducing the electrode into a tissue.

In another embodiment, the present invention can make use of one or more sensor mechanisms to provide feedback and/or control the ablation process. Sensor mechanisms can include sensors or detectors that detect and measure parameters such as temperature, current, voltage, impedance and the like. Certain embodiments of the present invention can include modifying the applied electric current at least partially based on a detected characteristic or a change in a detected characteristic. In one embodiment, for example, modification of the applied electric current can occur in response to a measured temperature, impedance, pH and the like. Modification can include, for example, modifying the voltage, frequency, etc. of the applied current and/or discontinuing application of the electric current, for example, where the ablation process or a stage thereof is determined to be completed.

A target tissue region can be located anywhere in the body where the tissue ablation methods of the present invention would be desired or beneficial. Target tissue is not limited to any particular type and non-limiting examples can include, e.g., breast tissue, prostate tissue, liver, lung, brain tissue, muscle, lymphatic, pancreatic tissue, colon, rectum, brochus and the like. The target tissue region will typically include a mass or solid portion of tissue. Typically, the target tissue region includes cancerous cells including, for example, a target tissue region including a solid tumor. The term "cancerous cell", as used herein, generally refers to any cells that exhibit, or are predisposed to exhibiting, unregulated growth, including, for example, a neoplastic cell such as a premalignant cell or a cancer cell (e.g., carcinoma cell or sarcoma cell), and are amenable to the ablation methods described herein. The volume of the tissue to be subject to the inventive methods can vary depending, for example, on the size and/or shape of the mass of cancerous cells, as well as other factors. Peripheral dimensions of the target tissue region can be regular (e.g., spherical, oval, etc.), or can be irregular.

Imaging systems and devices can be included in the methods and systems of the present invention. For example, the target tissue region can be identified and/or characterized using conventional imaging methods such as ultrasound, computed tomography (CT) scanning, X-ray imaging, nuclear imaging, magnetic resonance imaging (MRI), electromagnetic imaging, and the like. In some embodiments, characteristics of the tumor, including those identified using imaging methods, can also be used in selecting ablation parameters, such as energy application as well as the shape and/or geometry of the electrodes. Additionally, these or other known imaging systems can be used for positioning and placement of the devices and/or electrodes in a patient's tissues.

As set forth above, the electrode can be positioned within the target tissue region and the applied electric field can be selected to provide low-power or non-thermal (e.g., mild hyperthermia) ablation of target cells. The term "non-thermal ablation" as used herein generally refers to techniques of the present invention including the removal of or destruction of the function of tissue or cells of a tissue by application of an electric field, and where the energy application/delivery process occurs without a substantial increase in local tissue temperature beyond mild temperature increases due to mild or low-level hyperthermia, and without high-thermal effects (e.g., substantially above 10 degree increase in average tissue temperature in the target region) of energy application being a significant or primary means by which tissue ablation occurs. In some embodiments, a substantial increase in local tissue temperature can be avoided altogether, with no resulting apparent increase in temperature being detected in the target tissue region. In some embodiments, however, small changes/elevations in temperature in the target tissue region may occur, but will typically be no more than a few degrees C. above body temperature (e.g., less than about 10 degrees C., but typically no more than about 2 degrees above body temperature), and without the high-thermal effects (e.g., average tissue temperature above about 48-50 degrees C.) being the primary means by which tissue ablation occurs (e.g., no significant high-temperature, thermally-mediated, lethal protein denaturation). In some instances, energy delivery can be selected so as to deliver or establish low-level or mild increases in average tissue temperature of the target tissue/region, including delivery of mild hyperthermia to the tissue. As described above, mild hyperthermia may include an increase of the average tissue temperature up to about 10 degrees C. above body temperature (e.g., normal human body temperature of about 38 degrees C.). Thus, mild hyperthermia can include increased temperature up to about 48 degrees C., but will typically be controlled to prevent average tissue temperatures exceeding 50 degrees C. Target temperature ranges for energy delivery and resulting mild hyperthermia induction, according to the present invention, generally range from about 40-47 degrees C., and more typically about 42-45 degrees C. As target tissue temperatures rise above about 40-42 degrees C., the cytotoxic effects of energy delivery on cancerous cells of the target region is observably enhanced, possibly due to an additive and/or synergistic effect of current field and hyperthermic effects. Where hyperthermic effects are substantially maintained below about 48 degrees C., the energy delivery according to the present invention appears to more preferentially destroy cancerous cells compared to healthy or non-cancerous cells of the target tissue region. Where energy delivery induces tissue heating substantially in excess of about 45-48 degrees C., the preferential cytotoxic effects on cancerous cells begins to diminish, with more indiscriminate destruction of cancerous and non-cancerous cells occurring. Thus, a significant advantage of treatment methods according to the present invention includes the ability to precisely and accurately control energy delivery and induced hyperthermic effects, such that tissue hyperthermia can be accurately controlled and maintained in a desired temperature range(s)—e.g., temperature ranges selected for more targeted or preferential destruction of cancerous cells compared to non-cancerous cells.

Typically, the applied electric field includes a low-intensity, intermediate frequency alternating current. The intermediate frequency employed according to the present invention, for example, will be less than that typically required for excessive and indiscriminate frictional/resistance heating to tissue surrounding the electrode (e.g., less than about 400 kHz, preferably about 300 kHz or less). In one embodiment, for example, the electric current provides a voltage field less than about 50V/cm. In another embodiment, the electrical current includes a frequency between about 50 kHz and about 300 kHz.

The voltage field and/or the frequency of the applied current can be held constant during energy application or varied. One or more treatment phases can be applied, with each phase having selected treatment parameters (e.g., energy parameters, duration, etc.). In some embodiments, providing a non-constant or varying voltage and/or frequency by "scanning" across a given range may be desired, for example, to ensure that the optimal ablative voltage/frequency is applied to the target tissue region. In another embodiment, a particular voltage and/or frequency can be selected prior to energy application. In yet another embodiment, the voltage field can be turned "on" and "off" at a frequency height enough to keep the tissue relatively constant, and controlling the on/off duty cycle to more precisely control the temperature of the target tissue. Furthermore, the electrode(s) can be positioned within the target tissue region such that electrical current application occurs from within the target tissue, and the target tissue is ablated from the inside out. In one embodiment, electrode(s) are positioned within the target tissue region (e.g., tumor) and the applied electrical current provides an electric field extending radially outward from the electrode. In certain embodiments, such positioning can take advantage of tumor physiology, including, e.g., orientation of dividing/proliferating cells within a target tissue region, and ensure that the electric field provided by the electrode is substantially aligned with a division axis of a dividing cancerous cell, or otherwise established through a tissue volume in a plurality of directions.

Figure 2A:
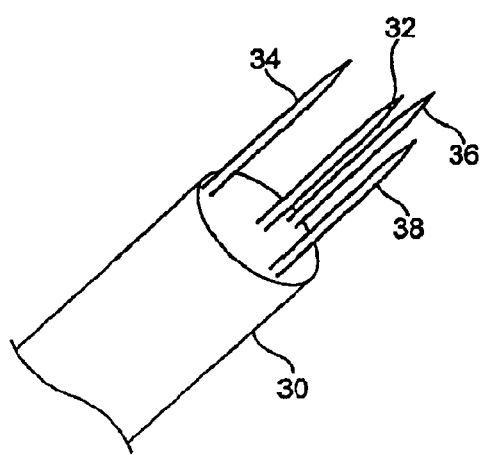
Figure 2D:
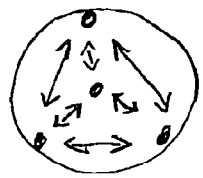
Figure 2B:
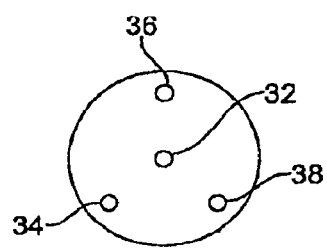

FIGS. 2A through 2C show a device having a plurality of electrodes according to another embodiment of the present invention. As shown, the device 30 includes a plurality of electrodes extending from the distal portion of the device. FIG. 2A shows a three dimensional side view of the device having the plurality of electrodes. FIG. 2B shows a top view of the device illustrating the electrode arrangement. The plurality includes a centrally positioned electrode 32 and outer electrodes 34, 36, 38 spaced laterally from the central electrode 32. The illustrated electrodes include substantially linear needle-like portions or needle electrodes. The electrodes extend from the distal portion of the device and are oriented to be substantially parallel with the longitudinal axis of the device 30. Additionally, each electrode is substantially parallel with other electrodes of the plurality. The plurality of electrodes substantially define the ablation volume, with the outer electrodes 34, 36, 38 substantially defining a periphery of the ablation volume and the electrode 32 positioned within or at about the center point of the defined periphery. Each of the electrodes can play different roles in the ablation process. For example, there can be changes in polarity and/or polarity shifting between the different electrodes of the device. As with other devices of the invention, electrodes can be electrically independent and separately addressable electrically, or two or more electrodes can be electrically connected, for example, to effectively function as one unit. In one embodiment, for example, outer electrodes 34, 36, 38 can be electrically connected and, in operation, include a polarity different from that of the inner electrode 32. As illustrated in FIG. 2C the electrodes 32 and 34, 36 of the device can include opposing charges (e.g., bipolar). In such an instance, the applied electrical current can provide an electrical field, as illustrated by the arrows, extending radially outward from the central electrode 32 and toward the peripherally positioned or outer electrode(s) 34, 36.

Electrodes of a plurality (e.g., as illustrated in FIGS. 2A-2C and elsewhere) can be activated in groups or pairs for establishing different current fields or field orientations through the target tissue. As shown in FIG. 2D, different pairs of electrodes can be differentially activated (e.g., in seriatim) so as to establish different current fields or field directions/orientations through a target tissue. Exemplary field directions/orientations are indicated by arrows.

In some embodiments, devices and/or systems of the present invention include electrically floating systems or systems designed to operate without an earth grounding. In some instances, it was observed that electrode configurations that were electrically floating in this manner allowed more accurate or controllable field application and/or delivery. The low-power requirements of systems according to certain embodiments allow more design options in configuring devices and systems that are electrically floating, as described, compared, for example, to known techniques such as thermal RF or microwave ablation, or high-voltage irreversible electroporation that require much higher powered energy delivery and corresponding power sources.

In some embodiments, probes of the current invention can include multiple groupings of electrodes positioned as "outer" electrodes, with each grouping defining a different ablation volume. For example, a probe can include a first group or plurality of electrodes forming a smaller ablation volume and a second group or plurality of electrodes forming a second and larger ablation volume, with the first volume being disposed in the second volume. A central electrode can be positioned at about a center point, which can be a center point of both of the volumes. During use, the center electrode can be of opposing polarity relative to electrodes of the first volume such that current flow and radial field distribution is established between the center electrode and electrodes of the first volume. In this manner, the device operates similar to embodiments having a single group of secondary or outer electrodes and, therefore, a single ablation volume, with current flow radially applied throughout the volume. In addition, current flow can also be established to extend radially through the larger second volume. Such current flow can be established, for example, by operating the central electrode and the electrodes of the second plurality at opposing polarities, e.g., to form a sort of circuit between the central and second plurality electrodes, or by operating the first plurality electrodes and the second polarity electrodes at opposing polarities, e.g., for circuit formation and current flow between electrodes of the first and second pluralities. Such "multi-layered" electrode embodiment may be useful, for example, for establishing the desired electric field and current flow through a larger volume of tissue (e.g., as defined by the second plurality of electrodes) that would be either not plausible or would be less efficient using a single group of outer electrodes.

Figure 3A:
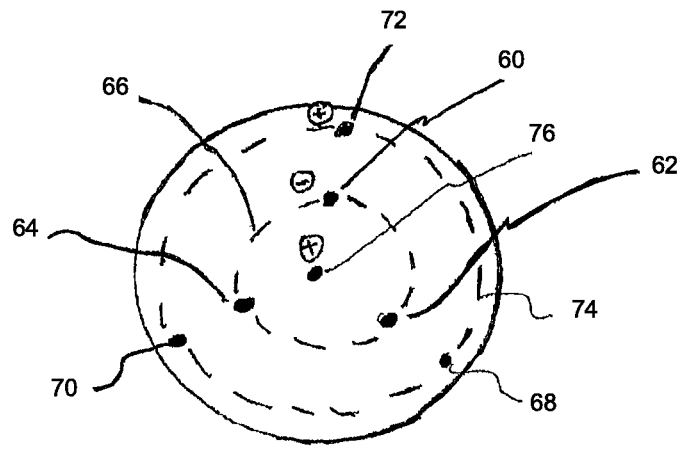
FIGS. 3A and 3B show frontal plan views of multi-layer electrode configurations according to embodiments of the present invention.
Figure 3B:
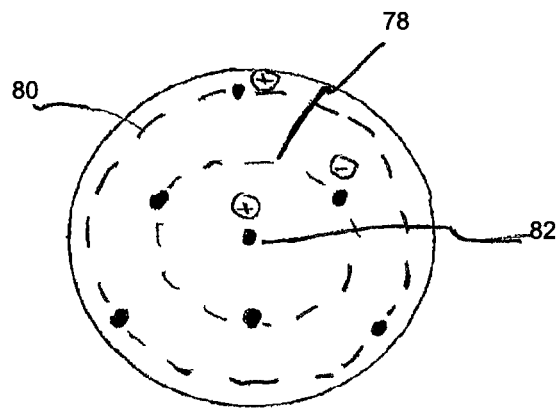

A multi-layer electrode configuration is illustrated with reference to FIGS. 3A and 3B. A top view of a multi-layer electrode configuration is shown in FIG. 3A. A first plurality of electrodes 60, 62, 64 are shown and substantially define a first volume 66, the outer perimeter or circumference illustrated by dashed lines connecting electrodes 60, 62, 64. A second plurality of electrodes 68, 70, 72 defines a larger second volume 74, with the outer perimeter shown in dashed lines connecting electrodes 68, 70, 72. Electrode 76 is positioned at a location at about a center point for both volumes 66 and 74. Energy application can be selected as described above. FIG. 3B illustrates a multi-layer electrode configuration according to another embodiment, where electrodes are off-set rather than being arranged along a more linear path as shown in FIG. 3A. Referring to FIG. 3B, a first group of electrodes defines a first volume 78, and a second group of electrodes defines a second volume 80. Center electrode 82 is positioned at about a center point of volumes 78, 80.

Figure 4A:
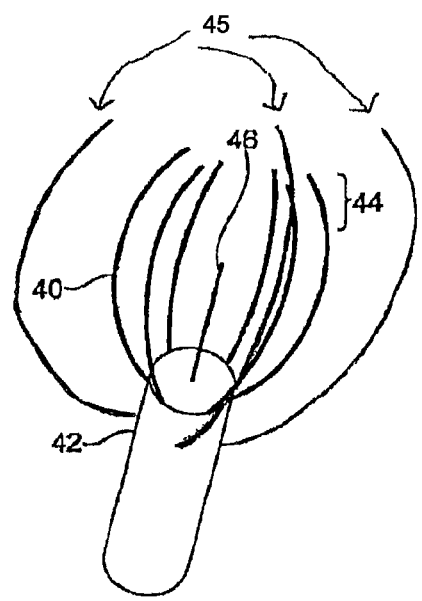
FIGS. 4A and 4B show a device having an electrode configuration including curved outer electrodes according to an embodiment of the present invention.
Figure 4B:
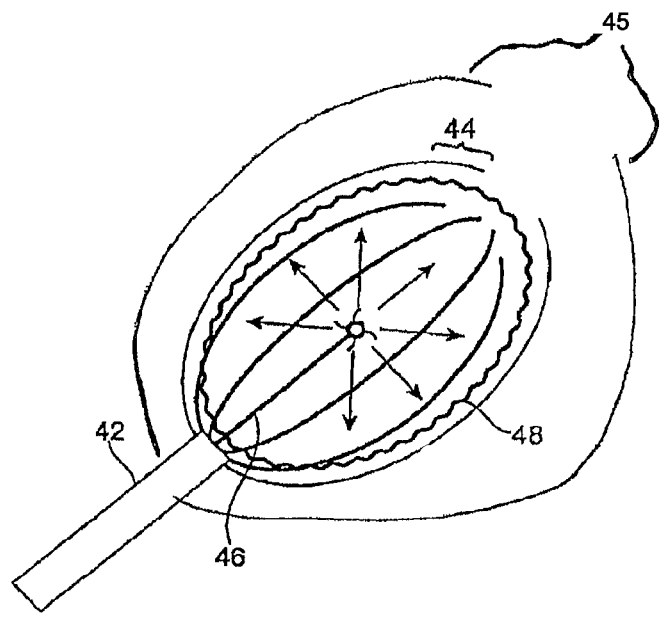

Another multi-layer electrode embodiment of a device of the invention is described with reference to FIGS. 4A and 4B, illustrating positioning of non-linear or curved electrodes as outer electrodes. The device 40 includes a plurality of electrodes at or extending from the distal end 42 of the device 40. The plurality of electrodes includes a first plurality of outer positioned electrodes 44 that are curved and substantially define a first ablation volume. An electrode 46 is positioned within the first volume defined by the outer electrodes 44 and spaced from the electrodes 44. The central electrode 46 is shown as being substantially linear and parallel with the longitudinal axis of the device 40, although other configurations will be available (e.g., curved, angled, etc.). A second plurality of electrodes 45 form a second ablation volume that is larger than the first volume, with the first volume substantially disposed in the second volume. FIG. 4B shows a target tissue 48 within the periphery defined by the first plurality of outer electrodes 44 with an electrical current being applied to the target tissue 48, and illustrating an oblong or oval ablation volume being defined by the first plurality curved electrodes 44. A target tissue region 48, such as a solid tumor, can essentially be encased within the first volume defined by the outer electrodes 44 as shown, or can extend beyond the outer perimeter of the first volume. Arrows illustrate an electric field extending outward and radially from the electrode 46 and in a plurality of different directions. The second plurality of electrodes 45 are shown and define a second volume, as described above.

Figure 5:
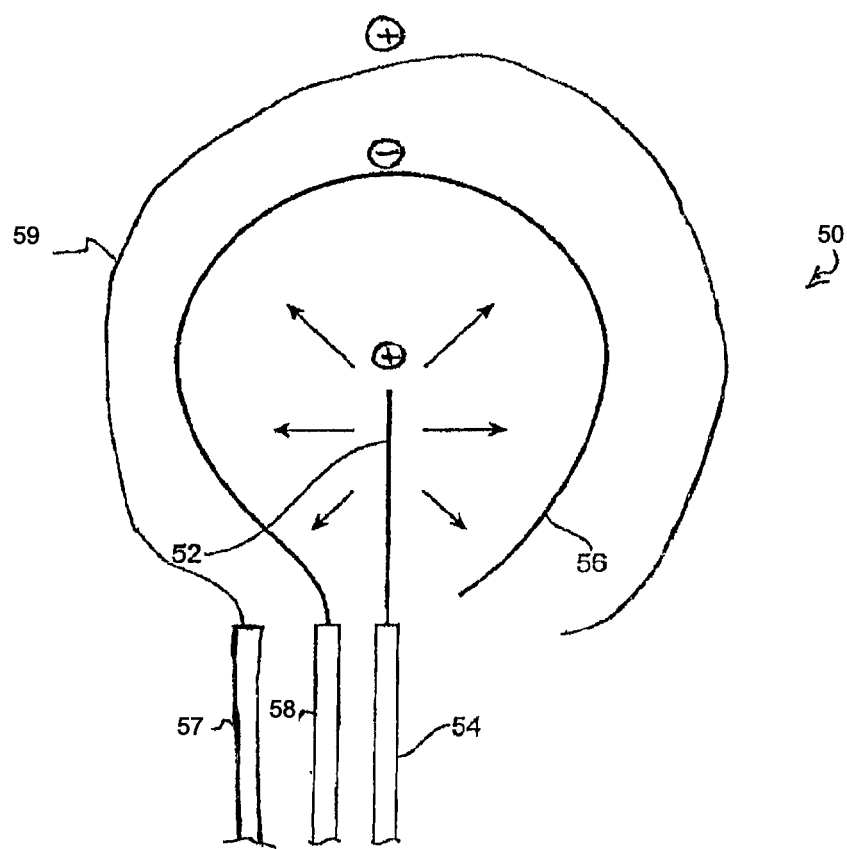
FIG. 5 illustrates a multi-layered electrode arrangement according to an embodiment of the present invention.

Electrodes of a device having a "multi-layer" configuration according to an embodiment of the present invention are described with reference to FIG. 5. The device 50 includes a substantially linear electrode 52 that is retractable in and out of a microtube 54 and an electrode 56 having a curved portion, the electrode retractable in and out of a microtube 58. Microtubes 58 and 54 can be included in a single delivery member, such as in a lumen(s) of a delivery catheter or can be independently arranged, e.g., for individually accessing and addressing a target tissue. Electrode 59 is deployable from microtube 57. As shown, electrode 56 extends circumferentially about center electrode 52 and defines a first current flow volume. Electrode 59 extends circumferentially about center electrode 52 and defines a second current flow volume larger than the first volume. The deployed electrode 56 is substantially disposed in the volume defined by electrode 59.

Figure 6A:
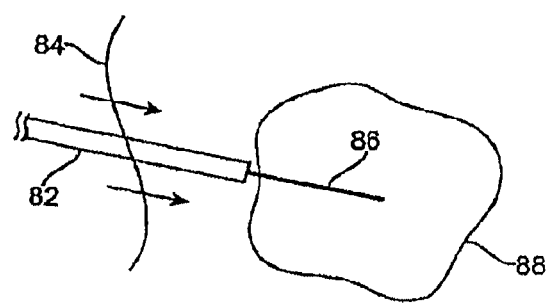
FIGS. 6A and 6B illustrate a method including positioning of an electrode in a target tissue, according to an embodiment of the present invention.
Figure 6B:
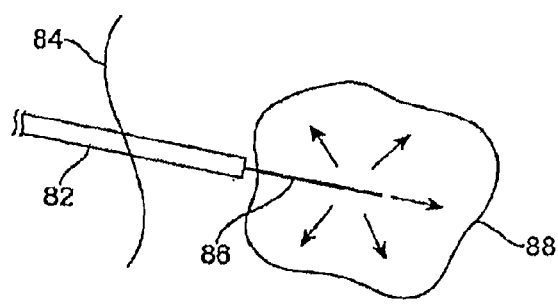

Referring to FIG. 6, positioning of a probe and electrodes thereof in a tissue of a patient is generally described. As shown in FIG. 6, a device 82 of the present invention can be advanced through the patient's tissue 84, and an electrode, e.g., electrode 86, of the device 82 positioned within a target tissue region 88 (e.g., tumor). Once the electrode is positioned in the target tissue region 88, electrical current is delivered to the target tissue region 88. As the electrode 86 is positioned within the target tissue region 88, the applied electrical current can provide an electric field that radiates outward and in a plurality of directions.

Figure 7A:
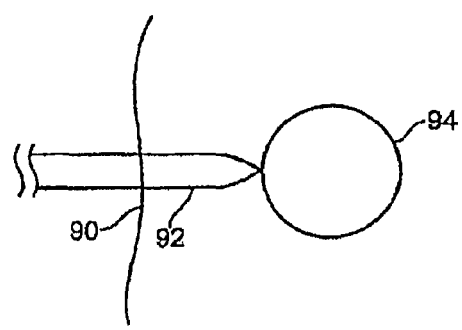
FIGS. 7A and 7B illustrate a method including deploying of multi-layered electrode configuration in a target tissue region, according to another embodiment of the present invention.
Figure 7B:
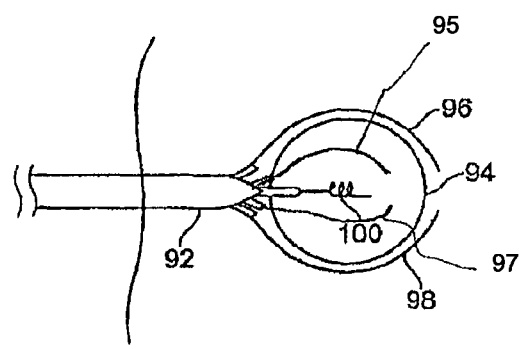

FIGS. 7A and 7B show use of a device of the present invention according to another embodiment of the present invention. As described above, the device 90 is advanced through the patient's tissue and the delivery member 92 positioned proximate to the target tissue region 94 (FIG. 7A). Once the delivery member 92 is positioned, a plurality of electrodes 95, 96, 97, 98, 100 can be deployed from the delivery member 92 (FIG. 7B). A first plurality of electrodes 95, 97 can be deployed to form a first volume, and a second plurality of outer electrodes 96, 98 can be deployed, e.g., at or around the perimeter of the target tissue region 94 to define a second volume, e.g., at about the margin of the target tissue region (e.g., tumor margin) and substantially define the ablation volume or target region. The inner electrode 100 is positioned within the ablation volumes and about at a common center location of the volumes.

The present invention can include various means of accessing or addressing a target tissue and positioning electrodes/probes for delivery of the described ablative treatment. Typically, positioning of a device of the invention will include a minimally invasive access and positioning techniques, including, e.g., access techniques commonly used with other types of tissue ablation (e.g., thermal RF ablation, microwave ablation, high-voltage electroporation, and the like). For example, devices of the invention can be introduced percutaneously through the skin and advanced through tissue and positioned at a target tissue. Though, addressing a target tissue and positioning of a device can occur in conjunction with more conventional surgical techniques.

As set forth above, certain embodiments of the present invention include positioning of an electrode within the target tissue region and applying an alternating electrical current, with the applied electrical current providing an electrical field that radiates outwardly from the positioned electrode. Electric field application in this manner was found to be highly effective in disrupting and destroying cancerous cells via low-power ablation and in the absence of a sustained high-temperature, thermal ablative effect (e.g., substantially in excess of 48 degrees C.). In certain embodiments, disruption of cancerous cells and resulting ablation according to the present invention effectively occurred where the electrical field provided by an electrode of an inventive device was applied in a radial field orientation, with fields presumably, based on tumor physiology, more substantially aligned with a division axis of a dividing cancerous cell or plurality of cells.

Furthermore, the electric field application as described was observed to be particularly effective in selectively disrupting and destroying the dividing cancerous cells, while having little or no effect on normal cells that were not exhibiting unregulated growth and proliferation. Without being bound by any particular theory, electric field application as described may specifically disrupt the cell division process (e.g., mitosis) or progression through the cell cycle, or a stage or process thereof (e.g., mitotic spindle formation, microtubule polymerization, cytoplasmatic organelle function or arrangement, cytokinesis, cellular osmotic balance or the like) and, therefore, more particularly effects cells exhibiting unregulated growth (e.g., cancerous cells) and progressing more rapidly through the cell cycle.

As mentioned above, selecting energy application to further generate a mild hyperthermic effect in the target tissue may be desirable and has been observed to enhance the cancer killing effects of the energy application according to the present invention. Thus, controlled tissue heating can also occur and may include tissue heating to about 2-10 degrees above body temperature, or heating tissue to about 40-48 degrees C., and preferably about 42-45 degrees C. Delivery of mild hyperthermia in this manner, together with establishing current field delivery as described, has been observed as surprisingly effective in destroying cancerous cells, and in some instances preferentially destroying cancerous cells compared to non-cancerous or healthy cells.

According to the present invention, a target tissue region can be ablated in whole or in part. It will be recognized that while it is generally desirable to ablate as much of the target region or tumor as possible, in some embodiments, methods can include ablation of a portion or less than the entirety of the target region. In some instances, partial tumor ablation can be sufficient to ultimately destroy or kill an entire tumor or cancerous tissue region.

As the ablation process is initiated, in some embodiments, the field intensity can be highest at the inner or central electrode and within tissue around and in close proximity to the inner or central electrode. As the ablation process progresses, cancerous cells near the inner electrode are observed to be destroyed or ablated first. The ablated cells effectively "liquefy" or assume properties of a low impedance, liquid-like material. The term "liquefy" is used herein for convenience and illustrative purposes, and does not necessarily imply any particular mechanism of ablation or cell death, which may include cell blebbing, apoptosis, lysis, or some other cellular process, and/or some combination thereof. Another possible cause of cell destruction may include disruption of cellular membrane integrity, e.g., including dielectric breakdown of one or more cellular membranes (see, e.g., below). The liquid-like material surrounds the central electrode and effectively enlarges the higher field intensity ablative area, with the highest field intensity ablative area being at the outer perimeter of the liquid-like material. Thus, the liquid-like material is said to become a "virtual electrode". As the ablation process progresses, the outer perimeter of the liquid-like material or "virtual electrode" expands, essentially ablating the target tissue region from the inside out. In some embodiments, target tissue regions were observed to be more pliable and soft or mushy following the ablation process. The ablated, liquid-like tumor tissue was eventually removed from the treatment site and/or absorbed by the surrounding tissue, and no longer detectible.

The ablation process, including the progress thereof, can be monitored by detecting the associated change in impedance in the ablated tissue. Once the outer perimeter of the ablated, liquid-like tissue reaches the outer electrodes defining the ablation volume, the impedance stabilizes or levels out. Thus, the progress of the ablation process can be monitored by measuring change in impedance, and electric field application discontinued once a change in impedance is no longer observed.

Feedback measurements can also be used to ensure that the ablation of the target cancerous cells occurs with tissue temperatures maintained in a desired temperature range. In certain embodiments it may be desirable to generate as much field intensity at the inner electrode as possible without causing an excessive hyper-thermal effect or high-temperature thermal ablation. Certain hyper-thermal effects would be observable and distinguishable from the desired non-thermal/mild hypertheric ablation of the present invention, since high-temperature thermal ablation would cause destruction of the surrounding cells without the "liquefying" effect described above. For example, if cell destruction is caused by a thermal ablation process, the impedance of the treated tissue may not decrease since the impedance of cells that are charred or become necrotic due to thermal effects typically increases. In one embodiment, non-thermal/mild hyperthermia ablation according to the present invention can include placement of a sensor, such as a thermocouple, within the target tissue region (e.g., proximate to the inner electrode), and selection of an applied field intensity as below the intensity that would cause high-temperature or undesirable thermal effects on the target cells.

In some embodiments, electrodes can be deployable from small, electrode guides or positioning tubes, e.g., microtubes or microcatheters, positionable in and advanceable from a distal portion of an ablation probe. The terms catheter or microcatheter, as used herein, refer generally to an elongate tube having a lumen. For example, an ablation probe of the present invention can include a distal portion or a delivery member having a lumen with an electrode aiming/positioning microtubes/microcatheters positioned within the lumen of the delivery member, with electrodes disposed in the microcatheters and deployable therefrom. Both microcatheters and electrodes can include a shape memory metal and include a preformed shape for deployment. In use, the distal portion of the probe can be positioned proximate to a target tissue, for example, by advancing the probe through a patient's tissue. Once in position, a microcatheter can be deployed from the delivery member and can act as an initial advancement or guide tube as advanced or deployed from the delivery member for initial aiming and/or positioning of the electrode disposed therein. Following advancement and positioning of the microcatheter, the electrode can be deployed from the microcatheter for desired positioning of the electrode at or in the target tissue region. The described "multi-phase" type of microcathter/electrode deployment configuration can provide more versatility and improved functionality in positioning of electrodes, and can permit a wider range of motion or positioning of an electrode in a tissue compared to other configurations, such as deployment of only an electrode alone. The described configuration was found to be well suited, for example, for positioning of outer electrodes (e.g., secondary electrodes) to define an ablation volume, particularly where electrodes are first advanced in a direction angling away from the delivery member and current flow center and then advanced in a direction that moves the electrode back toward the delivery member/center.

Figure 8A:
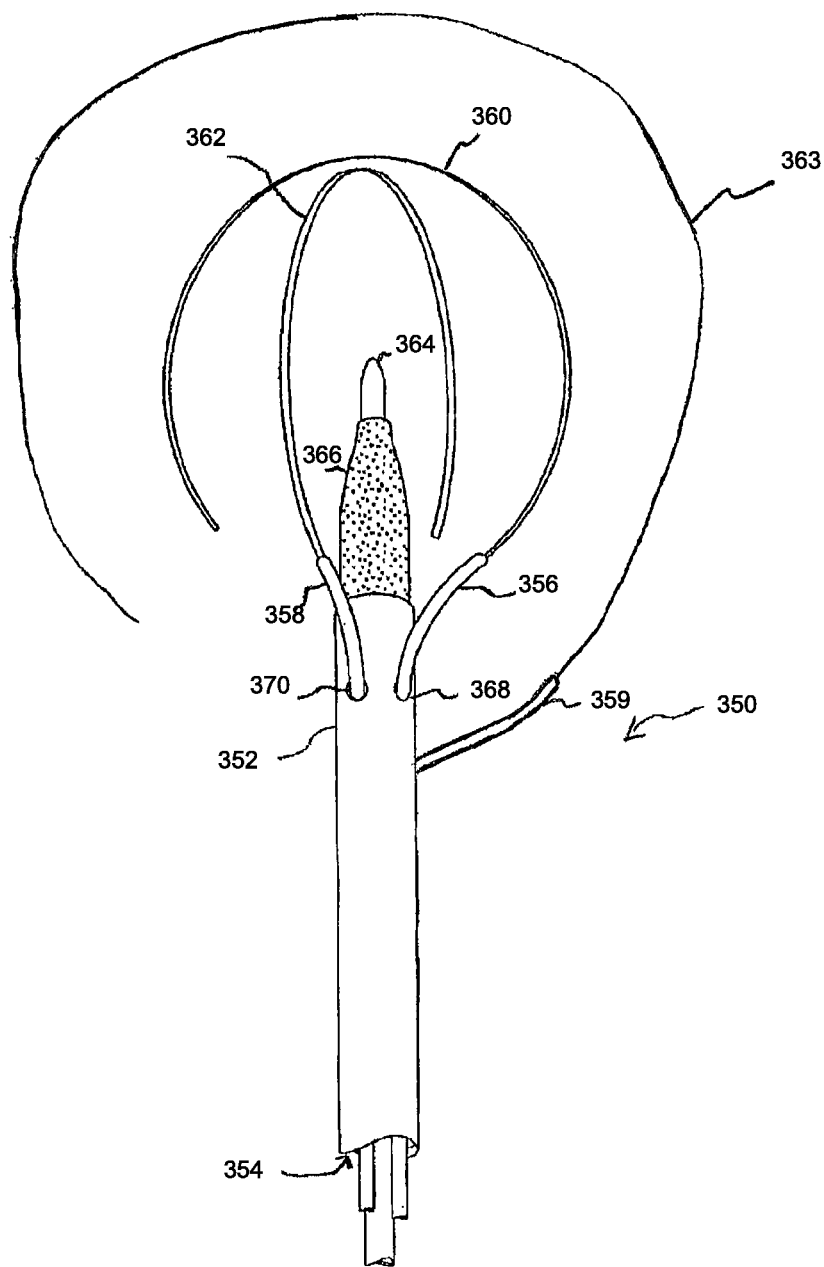
FIGS. 8A and 8B illustrate a multi-layer electrode configuration of an ablation probe, according to another embodiment of the present invention.
Figure 8B:
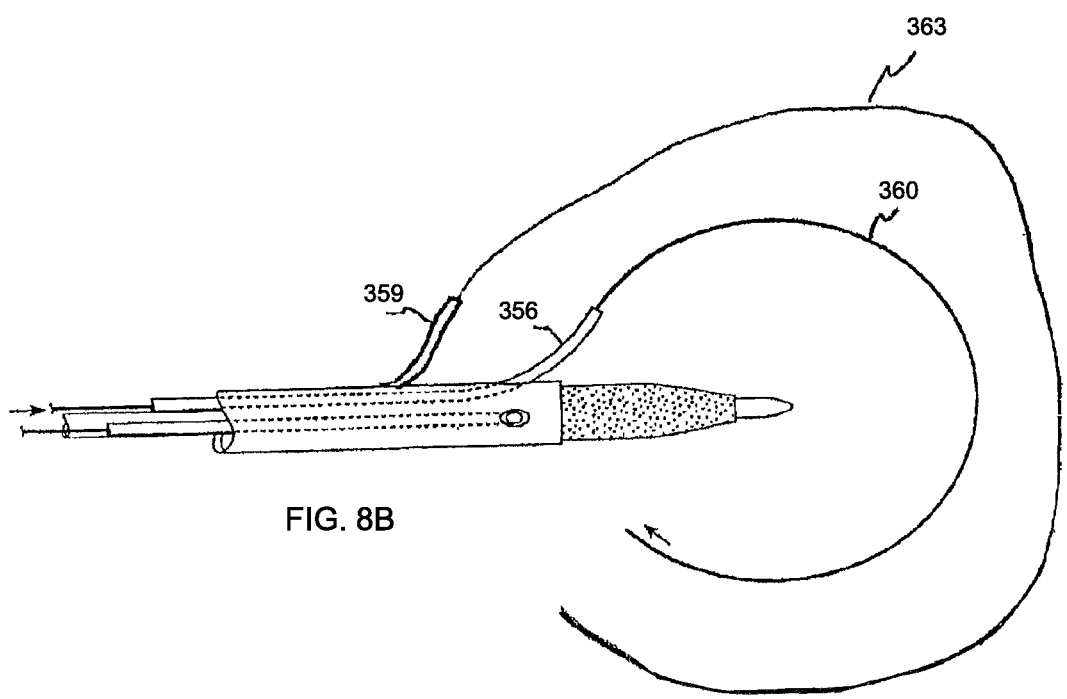

An ablation probe having deployable electrodes and microcatheters is described with reference to FIGS. 8A and 8B. Referring to FIG. 8A, the probe 350 includes a delivery member 352 that forms a distal portion of the probe 350, and includes lumen 354 in which microtubes/microcatheters 356, 358 can be positioned and deployed therefrom. The probe 350 is shown in a deployed state with microtubes 356, 358 advanced from lumen 354 of the delivery member 352 through openings 368, 370, respectively. Electrodes 360, 362 are shown advanced from microcatheters 356, 358, respectively. The deployed electrodes 360, 362 substantially define a first ablation volume with an electrode 364 positioned within the ablation volume. The centrally positioned electrode 364 can be deployable from a delivery member or can be substantially fixed or positioned in desired arrangement. As shown, the electrode 364 is positioned to form a distal tip of the probe and can be pointed or sharpened so as to more easily puncture through (e.g., percutaneously) and/or advance through a tissue. The probe can further include a tapered portion 366 (e.g., insulated portion) to facilitate advancement/positioning of the probe 350. The probe 350 is typically advanced to a target location with electrodes in a non-deployed state. Once the probe is positioned at a desired location, microcatheters 356, 358 can be advanced through openings 368, 370 the delivery member 352, e.g., for initial aiming of the electrodes in the desired direction and then electrodes 360, 362 deployed from the microcatheters 356, 358 for further positioning and formation of the first ablation volume. Microcatheter 359 and associated electrode 363 can be deployed in a similar manner to extend circumferentially about the center electrode 364 and the first ablation volume, and can thereby define a second ablation volume. Typically, the target tissue (e.g., cancerous tissue) will be at least partially contained in one or both ablation volumes. Current can be applied through the electrodes of the probe as described above such that an applied field radiates throughout the ablation volumes, thereby applying a field in radially and in a plurality of different directions. FIG. 8B shows a side profile view of deployed microcatheter 356 and electrode 360 defining a first volume, and deployed microcatheter 359 and electrode 363 defining a second volume. While multi-layer electrode probes are illustrated herein with a first and second volume, probes can include additional electrode layers so as to form additional volumes in a similar manner.

Figure 9:
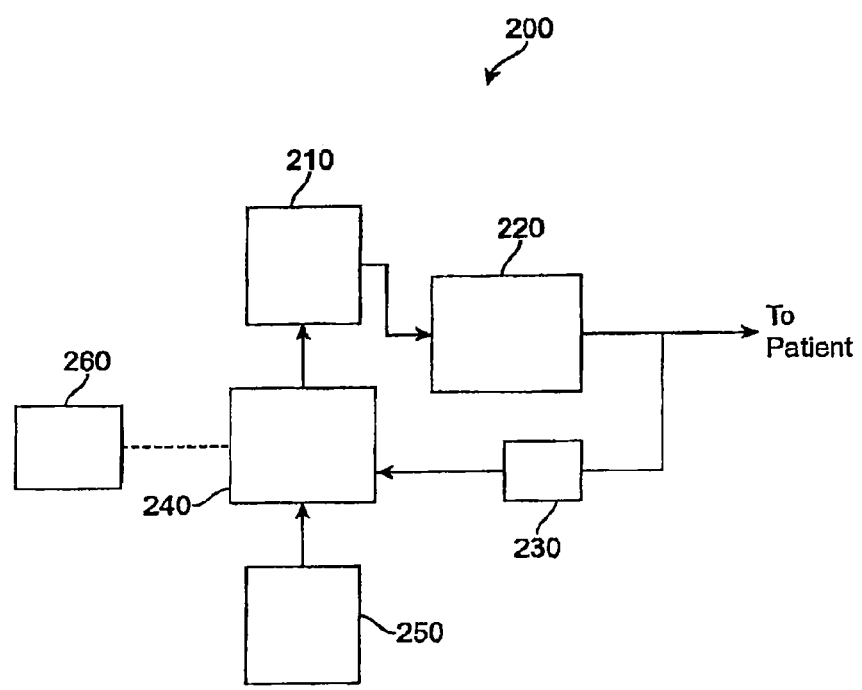
FIG. 9 illustrates a system according to an embodiment of the present invention.

A system according to an embodiment of the present invention is described with reference to FIG. 9. The system 200 can include incorporated therewith any device of the present invention for delivery of energy to the patient, and includes a power unit 210 that delivers energy to a driver unit 220 and then to electrode(s) of an inventive device. The components of the system individually or collectively, or in a combination of components, can comprise an energy source for a system of the invention. A power unit 210 can include any means of generating electrical power used for operating a device of the invention and applying electrical current to a target tissue as described herein. A power unit 210 can include, for example, one or more electrical generators, batteries (e.g., portable battery unit), and the like. One advantage of the systems of the present invention making use of non-thermal ablation techniques is the low power required for the ablation process. Thus, in one embodiment, a system of the invention can include a portable and/or battery operated device. A feedback unit 230 measures electric field delivery parameters and/or characteristics of the tissue of the target tissue region, measured parameters/characteristics including without limitation current, voltage, impedance, temperature and the like. One or more sensors (e.g., temperature sensor, impedance sensor, thermocouple, etc.) can be included in the system and can be coupled with the device or system and/or separately positioned at or within the patient's tissue. These sensors and/or the feedback unit 230 can be used to monitor or control the delivery of energy to the tissue. The power unit 210 and/or other components of the system can be driven by a control unit 240, which may be coupled with a user interface 250 for input and/or control, for example, from a technician or physician. The control unit 240 and system 200 can be coupled with an imaging system 260 (see above) for locating and/or characterizing the target tissue region and/or location or positioning the device during use.

A control unit can include a, e.g., a computer or a wide variety of proprietary or commercially available computers or systems having one or more processing structures, a personal computer, and the like, with such systems often comprising data processing hardware and/or software configured to implement any one (or combination of) the method steps described herein. Any software will typically include machine readable code of programming instructions embodied in a tangible media such as a memory, a digital or optical recovering media, optical, electrical, or wireless telemetry signals, or the like, and one or more of these structures may also be used to transmit data and information between components of the system in any wide variety of distributed or centralized signal processing architectures.

Components of the system, including the controller, can be used to control the amount of power or electrical energy delivered to the target tissue. Energy may be delivered in a programmed or pre-determined amount or may begin as an initial setting with modifications to the electric field being made during the energy delivery and ablation process. In one embodiment, for example, the system can deliver energy in a "scanning mode", where electric field parameters, such as applied voltage and frequency, include delivery across a predetermined range. Feedback mechanisms can be used to monitor the electric field delivery in scanning mode and select from the delivery range parameters optimal for ablation of the tissue being targeted.

Methods and techniques of the present invention may employ a single device or a plurality of devices. In one embodiment, for example, a device of the present invention can be positioned within a target tissue region as described above. A second device can then be positioned within the target tissue region or in another target tissue region, either of part of the same tumor or at a separate tumor. In one embodiment, for example, a first device is positioned in a target tissue region, and a second device can be positioned in the target tissue region, where the second device is positioned at an angle (e.g., 90 degree angle) relative the first device.

Systems and devices of the present invention can, though not necessarily, be used in conjunction with other systems, ablation systems, cancer treatment systems, such as drug delivery, local or systemic delivery, radiology or nuclear medicine systems, and the like. Similarly, devices can be modified to incorporate components and/or aspects of other systems, such as drug delivery systems, including drug delivery needles, electrodes, etc.

While embodiments of the present invention are discussed in terms of use for non-thermal ablation and destruction of cancerous cells as described above, in some instances systems and probes can be used and/or configured for delivering energy sufficient for other types of tissue ablation, such as thermal RF ablation, microwave ablation, irreversible electroporation via high-voltage direct current, and the like. For example, a system of the invention can include a power unit configured for delivery of energy suitable for any one or more types of tissue ablations. In fact, certain probe configurations have designs (e.g., electrode arrangements) that can provide improved delivery of a various types of tissue ablation, including, e.g., improved delivery of thermal RF ablation, and the like. And treatment according to methods of the present invention can include delivery of one or more types of tissue ablations for a given treatment.

In some instances, for example, treatment may include one or more ablation delivery modes, such as one mode where non-thermal/mild hyperthermic tissue ablation is delivered, which can precede or follow another ablation mode, such as high-temperature thermal RF tissue ablation or ionizing radiation. For example, in one embodiment, treatment can include delivery of non-thermal/mild hyperthermic tissue ablation followed by a shorter application or pulse of energy to produce a high-temperature thermal mediated effect, e.g., to help "sterilize" one or more components of the probe, e.g., for withdrawal from the target tissue through the entry track and reduced risk of tracking any potentially viable cancer cells through tissue during probe withdrawal.

In some embodiments, systems of the present invention can further include certain components and aspects for positioning and/or stabilizing probes and other components during the energy delivery process. For example, in instances where a phase of treatment, such as energy application, is expected to exceed more than a few minutes, it may be desirable to include a positioning or stabilizing structure to maintain a probe in a desired position/location without specifically requiring a user (e.g., surgeon) to hand-hold the probe. Thus a system can include a harness, belt, clamp, or other structure to maintain probe positioning. Systems can be designed for ambulatory use so as to allow for movement of the patient (e.g., shifting, walking, etc.) during treatment. In fact, the low-power requirements and corresponding design options (e.g., battery powered system) may make the current systems particularly well suited for use as an ambulatory system.

In some instances, it may be desirable to remove ablated tissue from the target tissue region at a stage of the ablation process described herein. For example, it has been observed that, in some instances, removal of ablated tissue can improve treatment and/or recovery of the subject, and possibly reduce stress and/or toxicity (e.g., local tissue toxicity, systemic toxicity, etc.) associated with the ablation process of the present invention. Various devices and methodologies can be utilized for removing the ablated tissue. In some instances, as described above, the ablated tissue can effectively "liquefy" or assume properties of a liquid-like material. The liquid ablated tissue can then be drained or removed from the target tissue region.

It is understood that the examples and embodiments described herein are for illustrative purposes only and that various modifications or changes in light thereof will be suggested to persons skilled in the art and are included within the spirit and purview of this application and scope of the appended claims. Numerous different combinations are possible, and such combinations are considered part of the present invention.

What is claimed is:

1. A method of delivering an electric field to a target tissue, comprising:
   positioning a first electrode to at least partially define a first treatment volume in the target tissue;
   positioning a second electrode to at least partially define a second treatment volume, wherein the first volume is disposed in the second volume;
   establishing a first electric field extending within the first volume and a second electric field extending within the second volume; and
   wherein the first electric field selectively destroys abnormally proliferating cells while leaving normal cells substantially intact within first treatment volume and the second electric field selectively destroys abnormally proliferating cells while leaving normal cells substantially intact within the second treatment volume.

2. The method of claim 1, wherein the first electrode and the second electrode curve around a field center.

3. The method of claim 2, wherein the field center comprises a central electrode positioned at about a location commonly central to the first and second volumes.

4. The method of claim 3, wherein the first electric field extends between the central electrode and the first electrode.

5. The method of claim 3, wherein the second electric field extends between the central electrode and the second electrode.

6. The method of claim 3, wherein the second electric field extends between the first electrode and the second electrode.

7. The method of claim 1, wherein establishing the first electric field destroys cancerous cells in the first volume.

8. The method of claim 7, wherein cancerous cell destruction comprises low-power, mild hyperthermic tissue ablation.

9. The method of claim 8, wherein the first electric field comprises a frequency between about 50 kHz and about 300 kHz, and an electric field strength less than about 50 V/cm.

10. The method of claim 1, wherein the first electric field and second electric field are established sequentially and at different times.

11. The method of claim 1, wherein the first electric field is established while the second electric field is established.

* * * * *